United States Patent [19]

Kniese et al.

[11] 4,045,492

[45] Aug. 30, 1977

[54] MANUFACTURE OF ALDEHYDES AND ALCOHOLS

[75] Inventors: Wilhelm Kniese, Limburgerhof; Hans Juergen Nienburg, Ludwigshafen, both of Germany

[73] Assignee: Badische Anilin- & Soda-Fabrik Aktiengesellschaft, Ludwigshafen (Rhine), Germany

[21] Appl. No.: 3,522

[22] Filed: Jan. 16, 1970

[30] Foreign Application Priority Data

Jan. 18, 1969 Germany ........................ 1902460

[51] Int. Cl.$^2$ .................. C07C 45/08; C07C 29/16
[52] U.S. Cl. ................... 260/604 HF; 260/598; 260/599; 260/632 HF
[58] Field of Search ............ 260/604 HF, 598, 599, 260/632 HF

[56] References Cited

U.S. PATENT DOCUMENTS

| 3,278,612 | 10/1966 | Greene | 260/632 |
| 3,594,425 | 7/1971 | Brader et al. | 260/604 HF |

FOREIGN PATENT DOCUMENTS

| 41,653 | 1/1966 | Japan | 260/604 |

OTHER PUBLICATIONS

Wagner, E. C.; J. Amer. Chem. Soc., vol. 56, pp. 1944–1946, 1934.

*Primary Examiner*—James O. Thomas, Jr.
*Assistant Examiner*—W. B. Lone
*Attorney, Agent, or Firm*—Keil, Thompson & Shurtleff

[57] ABSTRACT

Production of aldehydes and alcohols by oxo synthesis involving the reaction of olefinic compounds with carbon monoxide and hydrogen at elevated temperatures and under elevated pressures in the presence of amine-modified carbonyl complexes of cobalt or rhodium. Diamino diphenyl alkanes are used as modifying agents.

6 Claims, No Drawings

MANUFACTURE OF ALDEHYDES AND ALCOHOLS

This invention relates to an improved process for the production of aldehydes and alcohols by oxo synthesis involving the reaction of olefinically unsaturated compounds with carbon monoxide and hydrogen in the presence of amine-modified carbonyl complexes of cobalt or rhodium.

A widely used commercial process for the production of aldehydes and alcohols is oxo synthesis, in which olefins are reacted with carbon monoxide and hydrogen in the presence of cobalt carbonyl compounds as catalysts. This process has the drawback that high pressures, for example 280 atmospheres, must be used in order to prevent decomposition of the catalyst and deposition of cobalt in the reaction zone. The U.K. Pat. Specifications Nos. 988,941 and 988,943 reveal that oxo synthesis may be carried out at lower pressures than hitherto possible if the carbonyl complexes are modified with phosphines. However, this process suffers from the disadvantage that the inclusion of phosphines makes the recovery of the catalyst after the oxo reaction very expensive. Amines have also been proposed as modifying agents for catalysts to be used in the oxo reaction. U.S. Pat. Specification No. 992,136 and U.S. Pat. Nos. 2,820,059 and 3,231,621 reveal that monofunctional amines such as pyridines, dimethyl aniline and similar compounds are suitable as modifying agents for carbonyl complexes used in oxo synthesis. However, these amines have a relatively low boiling point and their separation from the oxo reaction mixture is thus difficult. Finally, U.K. Pat. Specification No. 1,152,503 discloses the use of polyamines, such as diethylene triamine or o-phenylene diamine, and also piperazine as modifying agents. In general, however, polyamines suffer from the drawback of requiring relatively high reaction temperatures, and their presence in the oxo reaction causes the formation of a disproportionately large amount of high-boiling components which is commercially undesirable and yield reducing.

It is an object of the invention to provide a process in which the reaction proceeds at low pressures and low temperatures. It is another object of the invention to provide a process in which there is no deposition of catalyst in the oxo reaction zone. It is yet another object of the invention to provide a process where the amines used may be readily isolated from the oxo reaction product and the catalyst may be readily recovered. It is a further object of the invention to provide a process in which fewer high-boiling components are formed than hitherto.

In accordance with the present invention these and other objects and advantages are achieved in an improved process for the manufacture of aldehydes and alcohols by oxo synthesis involving the reaction of olefinically unsaturated compounds with carbon monoxide and hydrogen at elevated temperatures and elevated pressures in the presence of amine-modified carbonyl complexes of cobalt or rhodium, the improvement comprising the use of diamino diphenyl alkanes as modifying agents.

Our new process is noteworthy, since U.S. Pat. No. 2,820,059 states in column 7 that bifunctional amines are not suitable for accelerating carbonyl-catalyzed oxo reactions. This statement is backed up to a certain extent by the fact that the use as modifying agents of polyamines in the process described in U.K. Patent Specification No. 1,152,503 cited above causes the formation of a disproportionately large amount of high-boiling residues.

We prefer to use aliphatic, cycloaliphatic or araliphatic olefinically unsaturated compounds of 2 to 20, preferably 2 to 16, carbon atoms. The preferred olefinically unsaturated compounds may have a number of double bonds, for example two non-conjugated double bonds, or they may have substituents which are inert under the reaction conditions, such as alkoxy groups of 1 to 4 carbon atoms. Particularly preferred starting materials are olefinically unsaturated compounds of hydrocarbon structure. Of particular commercial significance are olefins of 2 to 20, more particularly 2 to 16, carbon atoms, above all those having terminal double bonds. Examples of suitable olefinically unsaturated compounds are ethylene, propylene, hexene-1, octene-1, decene-1, hexadecene-1, tetradecene-1, cyclohexene, styrene, propenyl benzene, allyl alcohol, allyl methyl ether, olefin mixtures such as are produced in the oligomerization of propene and butene, for example so-called trimer propylene or co-dibutylene.

Carbon monoxide and hydrogen are in general used in a ratio, by volume, of from 5:1 to 1:5, particularly of from 2:1 to 1:2.

It is possible to use the olefinically unsaturated compounds and the mixture of carbon monoxide and hydrogen in stoichometric amounts. However, the mixture of carbon monoxide and hydrogen is advantageously used in excess, for example up to 500% molar.

The reaction is conveniently carried out at temperatures ranging from 60° to 200° C. Particularly good results are obtained on using temperatures ranging from 80° to 180° C, and particularly from 100° to 140° C. The reaction can be carried out at pressures ranging from 80° to 180° C, and particularly from 100° to 140° C. The reaction can be carried out at pressures ranging from, say, 1 to 300 atmospheres, but it is convenient to use pressures of from 10 to 200, preferably of from 20 to 100, atmospheres.

The reaction may be carried out without the additional use of solvents, in which case the olefinically unsaturated compounds themselves serve as solvents. But it is advantageous to use solvents which are inert under the conditions of the reaction, such as hydrocarbons, for example cyclohexane or xylene. In commercial practice it is convenient to use, as solvents, the same substances as will be formed as reaction products. The reaction is carried out in the presence of carbonyl complexes of cobalt or rhodium, modified by diamino diphenyl methanes having no hydrogen atoms attached to the nitrogen atoms. Of particular commercial significance are the carbonyl complexes of cobalt. We have found it advantageous for the atomic ratio of catalyst metal to nitrogen in the catalysts used to be in the range of 1:4 to 1:50, in particular of 1:10 to 1:20.

The diamino diphenyl alkanes used as preferred modifying agents are those of the general formula:

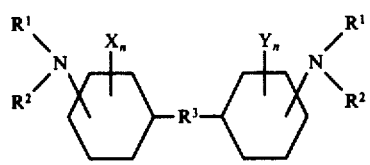

where $R^1$ and $R^2$ stand for alkyl radicals of 1 to 20 carbon atoms and in particular lower alkyl radicals 1 to 6 carbon atoms, or where $R^1$ and $R^2$ form, together with the adjacent nitrogen atom, a 5 to 7 membered heterocyclic ring, $R^3$ stands for an alkylene or alkylidene group of 1 to 4 carbon atoms, X and Y each independently stands for hydrogen or an alkyl group of 1 to 20 carbon atoms and in particular an alkyl group of 1 to 4 carbon atoms, an alkoxy group of 1 to 4 carbon atoms or a halogen atom and in particular a chlorine atom, and where n is 0, 1 or 2. In particularly preferred diamino diphenyl akanes of the above formula $R^1$ and $R^2$ stand for lower alkyl radicals of 1 to 4 carbon atoms, $R^3$ stands for an alkylene or alkylidene group of 1 to 3 carbon atoms, X and Y stand for hydrogen or lower alkyl radicals of 1 to 4 carbon atoms, in particular methyl radicals, and n is 0 or 1. Of particular commericial interest are diamino diphenyl methanes of the above formula in which $R^1$ and $R^2$ stand for lower alkyl radicals of 1 to 4 carbon atoms and X and Y stand for hydrogen atoms of methyl groups. Specific examples of suitable compounds are bis(4-dimethyl-aminophenyl)methane, bis(4-dimethylamino-3-methylphenyl)methane, bis(4-dimethylaminophenyl)propane-2,2, bis(4-aminophenyl)methane and bis(4-ethylaminophenyl)methane.

We prefer to use 0.1 to 2% by weight of catalyst (in terms of catalyst metal) bases on the amount of olefin used. Amounts ranging from 0.2 to 1% by weight are particularly advantageous. The catalysts may be preformed and fed to the oxo reaction as such. Alternatively, the catalyst starting materials, such as fatty acid salts of the metals and the said diamino diphenyl alkanes as modifying agents, may be fed to the reaction separately, in which case the catalyst will form in situ under the conditions of the reaction.

The process of the invention may be carried out, for example, by passing the olefinically unsaturated compounds and the mixture of carbon monoxide and hydrogen, optionally together with a suitable solvent, and the said catalysts in the ratio stated into a vertical high pressure tube at the bottom thereof and effecting the reaction under the stated conditions of pressure and temperature. After the pressure has been released, the reaction mixture is separated from the catalysts by distillation. The individual components of the reaction mixture are then isolated by known methods, for example by distillation. Unreacted olefins or unconsumed carbon monoxide/hydrogen mixture and the residue containing the catalyst may be recycled if desired.

Aldehydes and alcohols produced by the process of the invention are solvents or are suitable as intermediates in the production of plasticizers for polymers.

In the following Examples the parts are by weight unless otherwise stated, and their relationship to the party by volume is the same as that of the kilogram to the liter.

EXAMPLE 1

Into a high pressure tube packed with Raschig rings and of 500 parts by volume capacity there are metered 120 parts by volume of octene-1 per hour. Each kilogram of the octene-1 contains 50 g. of bis(4-dimethylaminophenyl)methane and 6.9 g. of cobalt ethyl hexanoate (85 % by weight). At the same time there is metered a mixture of carbon monoxide and hydrogen (1:1 by volume) at such a rate that a pressure of 40 atmospheres is maintained. Both of the streams enter the tube at the bottom thereof. The reaction temperature is held at 120° C. 107 parts of material are discharged per hour, the discharged material being brownish red in color and having a refractive index $n_D^{20}$ of 1.4290. 250 parts of the discharged material are separated in a Sambay evaporator at 150° C and 10 mm. of mercury pressure into 222 parts (88.8%) of distillate and 25 parts (10%) of residue. The distillate contains no amine. 200 parts of the distillate are fractionally distilled in a column, giving 35.3 parts (17,7%) of first runnings having a boiling point below 50° C (10 mm) and a refractive index $n_D^{20}$ of 1.4102 and comprising 79% octenes and 10% octane; 143.8 parts of main fraction (71.9%) having a boiling point of 64° to 70° C (10 mm) and a refractive index $n_D^{20}$ of 1.4210 and comprising 89% $C_9$ aldehydes and 10% $C_9$ alcohols. There remain 19.8 parts of residue and hold-up (9.9%).

EXAMPLE 2 (COMPARATIVE)

Example 1 is repeated except that octene-1 is used which contains per kilogram only 6.9 g of cobalt ethylhexanoate (85% by weight). 87.5 parts of material are discharged per hour, the discharged material being violet in color and having a refractive index $n_D^{20}$ of 1.4078. 200 parts of the discharged material are fractionally distilled and give 195.6 parts (97.8% by weight) of first runnings having a boiling point of up to 46° C (10 mm) and a refractive index $n_D^{20}$ of 1.4078 and comprising 98% octenes and 1% octane, and 4.2 parts (2.1%) of residue and hold-up.

EXAMPLE 3 (COMPARATIVE)

Example 1 is repeated except that octene-1 is used which contains per kilogram 6.9 g of cobalt ethyl hexanoate (85% by weight) and 21 g of o-phenylene diamine. 87.1 parts of material having a refractive index $n_D^{20}$ of 1.4106 are discharged per hour. 220 parts of the discharged material are separated by distillation in a Sambay evaporator (10 mm of mercury, 150° C) into 213 parts (97%) of distallate and 6 parts (2.7%) of residue. Analysis by gas chromatography shows the distillate to contain 87% octene, 1.5% octane, 10% $C_9$ aldehydes and less than 1% $C_9$ alcohols.

EXAMPLE 4

200 g of octene-1, 0.6 g of dicobaltoctacarbonyl and 0.08 gram equivalents of bis(4-dimethylaminophenyl)methane are placed in a 1 liter autoclave of stainless steel. The autoclave is heated under slight synthesis gas pressure (carbon monoxide:hydrogen = 1:1) at 120° C, and synthesis gas is then pumped in until the pressure is 40 atmospheres. The commencement of the reaction is discernible by a fall in pressure. The pressure is maintained at 40 atmospheres by introducing further quantities of synthesis gas as required. Two hours after no further pressure drop is noted the autoclave is allowed to cool and the pressure on the reaction mixture is released. The reaction product (246 g) is distilled in a Sambay evaporator (at 150° C and 10 mm of mercury), to give 83.2% by weight of distillate (based on the reaction mixture). Analysis by gas chromatography shows the distillate to contain 87.7% of nonanal, 5.1% nonanol and 4% of octene.

The following Table illustrates further comperative Examples carried out in a manner similar to that described in Example 4 using in each case 0.08 gram equivalents of other amines as modifying agents.

TABLE

| Ex. | Added amine | Reaction mixture (g) | Distillate (% by wt.) | Composition of Distillate in % | | |
|---|---|---|---|---|---|---|
| | | | | nonanal % | nonanol % | octene % |
| 5 | bis(4-dimethyl-aminocyclohexyl) methane | 210 | 94 | <1 | <1 | 98 |
| 6 | bis(4-dimethyl-aminocyclohexyl) propane-2,2 | 191 | 87,5 | <1 | <1 | 98 |
| 7 | 2,2'-bipyridyl | 203 | 76 | <1 | <1 | 98 |
| 8 | triethylamine | 209 | 96 | 8.5 | <1 | 85 |
| 9 | N,N'-tetramethyl-ethylene diamine | 205 | 98 | <1 | <1 | 98 |
| 10 | hexamethylene diamine | 200 | 96 | <1 | <1 | 98 |
| 11 | bis(β-aminoethyl) amine | 197 | 98 | <1 | <1 | 98 |
| 12 | piperazine | 196 | 98 | <1 | <1 | 98 |

We claim:

1. In a process for the production of aldehydes and alcohols by oxo synthesis involving the reaction of an olefin having 2 to 20 carbon atoms with carbon monoxide and hydrogen at pressures ranging from 1 to 300 atmospheres in the presence of an amine and a carbonyl complex of cobalt, the improvement comprising using as said amine a diamino diphenyl alkane having the formula

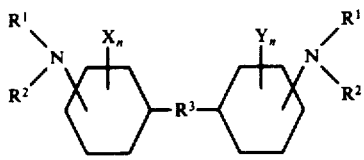

where $R^1$ and $R^2$ stand for alkyl radicals of 1 to 4 carbon atoms, $R^3$ stands for an alkylene or alkylidene radical of 1 to 3 carbon atoms, X and Y respectively stand for hydrogen or methyl, and $n$ is 0,1 or 2 at temperatures in the range of 100°-140° C.

2. A process as claimed in claim 1 wherein pressures ranging from 10 to 200 atmospheres are used.

3. A process as claimed in claim 1 wherein pressures ranging from 20 to 100 atmospheres are used.

4. A process as claimed in claim 1 wherein the atomic ratio of cobalt metal to nitrogen contained in the diamino diphenyl alkanes ranges from 1:4 to 1:50.

5. A process as claimed in claim 1 wherein said olefin is a member selected from the group consisting of ethylene, propylene, hexene-1, octene-1, decene-1, hexadecene-1 and tetradecene-1.

6. A process as claimed in claim 1, said olefin being a mono-olefin having a terminal double bond.

* * * * *